(12) United States Patent
Ivarsson et al.

(10) Patent No.: US 10,487,097 B2
(45) Date of Patent: Nov. 26, 2019

(54) **4,6-DI-(O-THIOPHOSPHATE)-INOSITOL-1,2,3,5-TETRA-O-SULFATE FOR *C. DIFFICILE* INFECTION**

(71) Applicant: ETH Zurich, Zurich (CH)

(72) Inventors: Mattias Ivarsson, Zurich (CH); Jean-Christophe Leroux, Zurich (CH); Bastien Castagner, Montreal (CA)

(73) Assignee: ETH ZURICH, Zurich (CH)

( * ) Notice: Subject to any disclaimer, the term of this patent is extended or adjusted under 35 U.S.C. 154(b) by 0 days.

(21) Appl. No.: 16/060,972

(22) PCT Filed: Dec. 12, 2016

(86) PCT No.: PCT/EP2016/080545
§ 371 (c)(1),
(2) Date: Jun. 11, 2018

(87) PCT Pub. No.: WO2017/098033
PCT Pub. Date: Jun. 15, 2017

(65) Prior Publication Data
US 2018/0362554 A1    Dec. 20, 2018

(30) Foreign Application Priority Data

Dec. 11, 2015 (EP) .................................... 15199681
Apr. 7, 2016 (EP) .................................... 16164300

(51) Int. Cl.
*C07F 9/177* (2006.01)
*A61P 31/04* (2006.01)

(52) U.S. Cl.
CPC ............ *C07F 9/177* (2013.01); *A61P 31/04* (2018.01)

(58) Field of Classification Search
CPC ...................................................... C07F 9/177
See application file for complete search history.

(56) References Cited

U.S. PATENT DOCUMENTS 9,200,015 B2    12/2015   Savidge et al.

FOREIGN PATENT DOCUMENTS

EP    0269105    6/1988
WO   2013045107   4/2013

OTHER PUBLICATIONS

Estelle Durantie Et Al: "New Paradigms for the Chiral Synthesis of Inositol Phosphates" Chembiochem—A European Journal of Chemical Biology, vol. 16, No. 7, Mar. 12, 2015, pp. 1030-1032.
E Durantie: "Chemical Synthesis of Biomolecules Analogs: Inositol Phosphate/Sulfate Hybrids and Fluorinated Carbohydrates", DISS. ETH No. 22532, Jan. 1, 2015, pp. 1-84.
Elliott, T., Slowey, A., Ye, Y. and Conway, S. (2012). The use of phosphate bioisosteres in medicinal chemistry and Chemical biology. Med. Chem. Commun., 3(1), pp. 735-751.
Hamblin, M., Flora, J. and Potter, B. (1987). myo-Inositol phosphorothioates, phosphatase-resistant analogues of myo-inositol phosphates. Synthesis of DL-myo-inositol 1,4-bisphosphate and DL-myo-inositol 1,4-bisphosphorothioate. Biochem J., 246(3), pp. 771-774.

*Primary Examiner* — Karen Cheng
(74) *Attorney, Agent, or Firm* — JMB Davis Ben-David

(57) ABSTRACT

The present invention relates to inositol bisthiophosphates-tetrakissulfates, particularly for use in treating symptoms associated with *Clostridium difficile* infection.

6 Claims, 4 Drawing Sheets

4,6-DI-(O-THIOPHOSPHATE)-INOSITOL-1,2,3,5-TETRA-O-SULFATE FOR *C. DIFFICILE* INFECTION

CROSS-REFERENCE TO RELATED APPLICATIONS

This is the U.S. National Stage of International Patent Application No. PCT/EP2016/080545 filed on Dec. 12, 2016, which was published in English under PCT Article 21(2), and which in turn claims the priority of European Patent Application Nos. 15199681.6 filed Dec. 11, 2015 and 16164300.2 filed Apr. 7, 2016.

FIELD

The present invention relates to 4,6-di-(O-thiophosphate)-inositol-1,2,3,5-tetra-O-sulfate and its use as an enteric activator of *Clostridium difficile* toxin in prevention and therapy of the toxic symptoms associated with *C. difficile* infection.

BACKGROUND OF THE INVENTION

Infections with *Clostridium difficile* can lead to severe, even life-threatening diarrhoea. The symptoms are caused by two toxins synthesized by *C. difficile*, TcdA and TcdB. The toxins can enter the cells lining the colon, where they are activated by cytosolic inositol hexakisphosphate (IP6) and exert their toxic function. One suggested therapeutic intervention is to activate the toxins in the extracellular space of the colon lumen. The activated toxins are no longer able to enter the colon cells, and within the colon lumen they cannot exert their toxic function. Thus, activation of the toxins within the colon lumen renders the toxins harmless for the affected patient.

IP6 cannot be used for therapeutic intervention, because it precipitates due to the high calcium concentration in the colon lumen.

WO2013045107A1 shows PEG-modified inositol phosphate compounds and mixed inositol phosphate-sulfate compounds and their use in activation of *C. difficile* toxin activation. The activity of the compounds shown therein is promising, however improvements upon the results related therein would be of advantage. Thus, the problem underlying the present invention is to provide activators of *C. difficile* toxin that exhibit stronger activity at high calcium concentration.

This problem is solved by the subject matter of the independent claims.

DESCRIPTION OF THE INVENTION

During an investigation of the compound class first shown in WO2013045107A1, it was surprisingly found that a small subset of mixed inositol tetrakissulfate bisthiophosphate compounds is far superior in effect to previously investigated mixed sulfate-phosphate compounds (see FIG. 1).

According to a first aspect of the invention, a compound characterized by the general formula (I)

$$\text{(I)}$$

(cyclohexane ring with six X substituents)

is provided, wherein two out of six X are $OPSO_2^{2-}$ and the remaining X are $OSO_3^-$.

The straight lines in formula I are meant to indicate that the stereochemistry of the individual ring carbon atoms is undefined. The formula is meant to encompass any diastereomer.

In certain embodiments, the compound is characterized by the general formula (IIa) or (IIb)

$$\text{(IIa)}$$

(inositol ring with $OSO_3^-$, $^-O_3SO$, $OSO_3^-$, $^{2-}O_2SPO$, $OSO_3^-$, $OPSO_2^{2-}$)

$$\text{(IIb)}$$

(inositol ring with $OSO_3^-$, $^-O_3SO$, $OSO_3^-$, $^{2-}O_2SPO$, $OSO_3^-$, $OPSO_2^{2-}$)

According to a second aspect of the invention, the compound as specified by formulae (I), (II), (IIa) or (IIb) is provided for use as a medicament in the therapy or prevention of a disease.

According to a third aspect of the invention, the compound as specified by formulae (I), (IIa) or (IIb) is provided for use in the therapy or prevention of *C. difficile* infection, or in the therapy or prevention of symptoms associated with *C. difficile* infection.

The compounds according to the invention do not need to penetrate mammalian or bacterial membranes to be active. In addition, the compounds according to the invention are unlikely to put selective pressure on the *C. difficile* bacteria, thus avoiding problems related to resistance.

According to a fourth aspect of the invention, a dosage form comprising the compound as specified by formulae (I), (IIa) or (IIb) is provided, particularly for use in the therapy or prevention of *C. difficile* infection, or in the therapy or prevention of symptoms associated with *C. difficile* infection.

In certain embodiments, the dosage form is a peroral formulation, particularly a tablet, capsule, lozenge, powder, solution or syrup.

According to an alternative aspect of the invention, the compound as specified in the above aspects of the invention is provided as a medicament, particularly a medicament formulated for use in the prevention or therapy of symptoms associated with *C. difficile* infection.

In certain embodiments, the medicament comprises the compound as specified in the above aspects of the invention alone or together with one or more pharmaceutically acceptable excipients or carriers.

The medicament may be administered alone or in combination with one or more therapeutic agents, particularly in combination with an antibacterial drug, more particularly in combination with an antibacterial drug selected from the group comprising (by way of non-limiting examples) metronidazole, vancomycin or fidaxomicin.

According to yet another aspect of the invention, a method of treatment or prevention of symptoms associated with *C. difficile* infection is provided, comprising the administration of the compound as specified by formulae (I), (IIa) or (IIb) to a subject in need thereof. Administration may be effected by any of the aforementioned means.

The compound may be given to a patient already diagnosed with *C. difficile* infection, or to a patient being suspected of suffering from *C. difficile* infection. Alternatively, the compound may be used as a prophylactic for patients that are at risk of contracting the infection, such as patients under treatment with antibacterial drugs in hospital settings.

According to yet another aspect of the invention, a method of treatment of *C. difficile* infection is provided, comprising the administration of an antibacterial drug, particularly metronidazole, vancomycin or fidaxomicin in combination with the compound as specified by formulae (I), (IIa) or (IIb) to a subject in need thereof.

SHORT DESCRIPTION OF THE FIGURES

EXAMPLES

Example 1: Synthesis of Compound (IIa)

Figure 1:
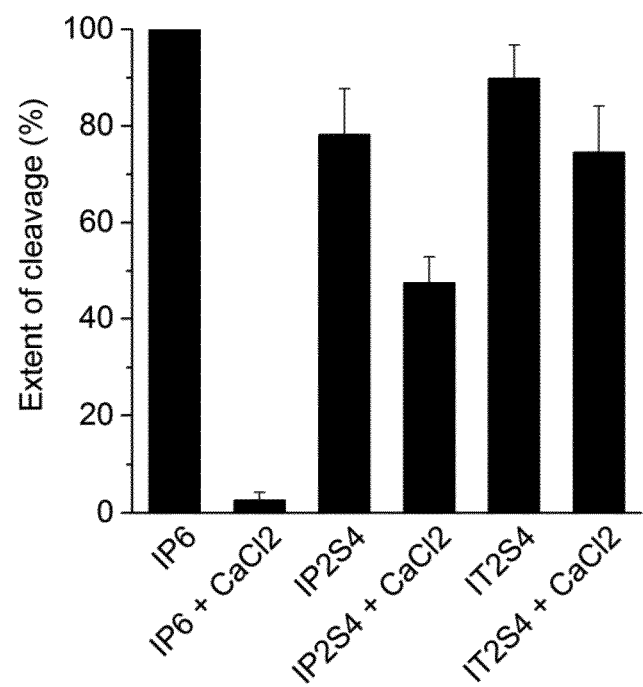
FIG. 1 shows the extent of cleavage of TcdB in the presence and absence of $Ca^{2+}$ (10 mM) for IP6, IP2S4 and activator compound IT254 (IIa).

The synthesis followed the sequence depicted in the scheme below:

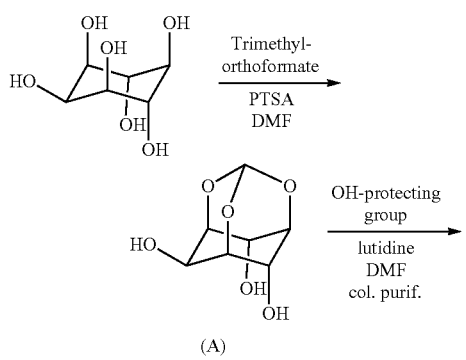

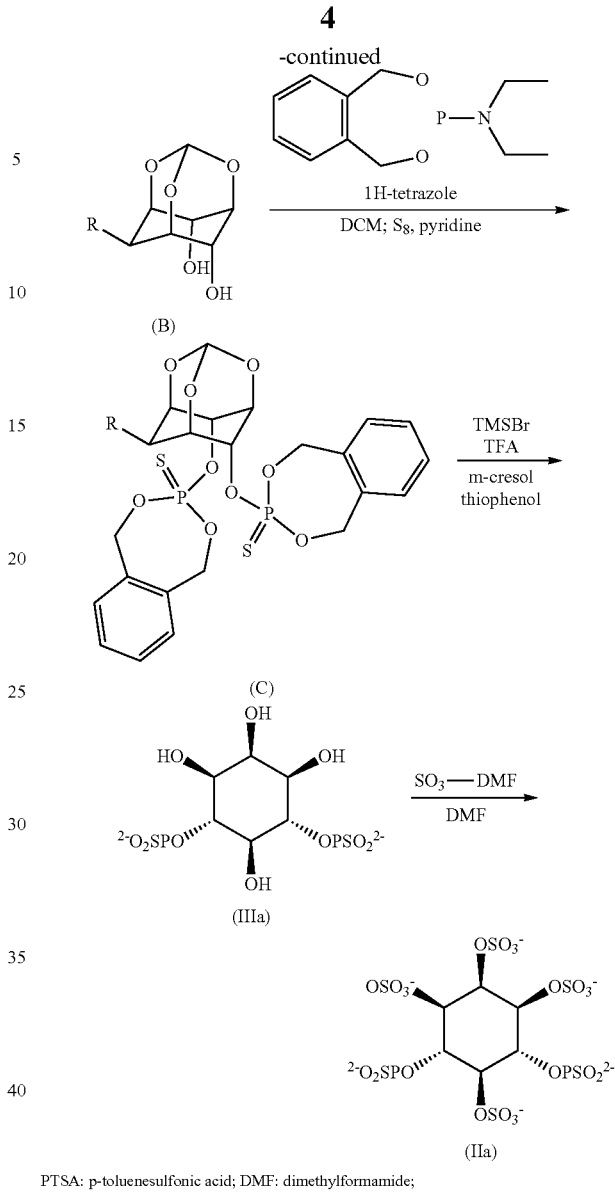

PTSA: p-toluenesulfonic acid; DMF: dimethylformamide;
TBDMSCl: tert-butyldimethylsilyl chloride;
DCM: dichlormethane;
S8: elemental sulphur;
pyr.: pyridine;
TMSBr: trimethylsilyl bromide,
TFA: trifluoroacetic acid Phosphorylation The known 2-tertbutyldimethylsilyl inositol orthoformate was co-evaporated 3× with toluene and dissolved in dichlormethane (DCM). 1H-tetrazole (4 eq.) followed by phosphoramidite (8 eq.) were added to the reaction and stirred overnight. Pyridine, followed by crushed sulphur flakes (20 eq.) were added to the reaction and stirred overnight. The resulting crude mixture was diluted with DCM and washed with saturated $NaHCO_3$, dried with $Na_2SO_4$, filtered and concentrated. The product was purified by flash chromatography with DCM in toluene.

$^1$H-NMR (400 MHz; $CDCl_3$): δ 7.35-7.29 (m, 4H), 7.15 (dd, J=6.6, 2.1 Hz, 2H), 7.07-7.04 (m, 2H), 5.54 (d, J=1.1 Hz, 1H), 5.45-5.41 (m, 2H), 5.30-4.97 (m, 8H), 4.51-4.49 (m, 1H), 4.33-4.32 (m, 2H), 4.27 (d, J=1.3 Hz, 1H), 0.93 (s, 9H), 0.13 (s, 6H); $^{31}$P-NMR (162 MHz; $CDCl_3$): δ 70.1

Deprotection

The following deprotection conditions are in analogy to the synthesis published in the Journal of the American Chemical Society [*JACS* 2005, 127, 5288].

Starting material (50 mg) was treated with thiophenol (300 µl), m-cresol (300 µl), trifluoroacetic acid (1.8 ml). Then added TMSBrOH slowly (360 µl). Stirred 2 h at room temperature. Evaporated twice from toluene. Diluted with DCM, and ca. 5 ml water. Neutralized with 1N NaOH. Poured aqueous layer (slightly cloudy) directly on SolEx C18 cartridge (Thermofisher, 1 g, 6 ml). Eluted with water. In some cases some aromatic impurities were found but would precipitate over time in water and could be filtered-off.

$^{1}$H-NMR (500 MHz; D$_2$O): δ 4.36 (q, J=9.6 Hz, 2H), 4.02 (t, J=2.7 Hz, 1H), 3.64 (dd, J=9.7, 2.8 Hz, 2H), 3.50 (t, J=9.3 Hz, 1H).

$^{31}$P-NMR (203 MHz; D$_2$O): δ 45.7

Sulfation

The sulfation reaction of the thiophosphate has to be performed carefully because the thiophosphate is eventually converted to the phosphate under the reaction conditions. We thus monitored the sulfation carefully and saw that the reaction was complete after ca. 30 min. and that no decomposition could be observed in this time. Thus, sulphurtrioxide dimethylformamide (SO$_3$-DMF) complex (12 eq.) was added to a suspension of inositol phosphate in DMF and the reaction was stirred 35 min. The reaction was quenched by adding 1N NaOH, until ca. pH 8 followed by ca. 3 ml methanol (MeOH) to precipitate salts. The solid was purified by Sephadex LH-20 column, eluting with water.

$^{1}$H-NMR (500 MHz; D$_2$O): δ 5.06 (s, 1H), 5.04-4.98 (m, 4H), 4.79-4.76 (m, 1H).

$^{31}$P-NMR (203 MHz; D$_2$O): δ 44.5

Figure 2:
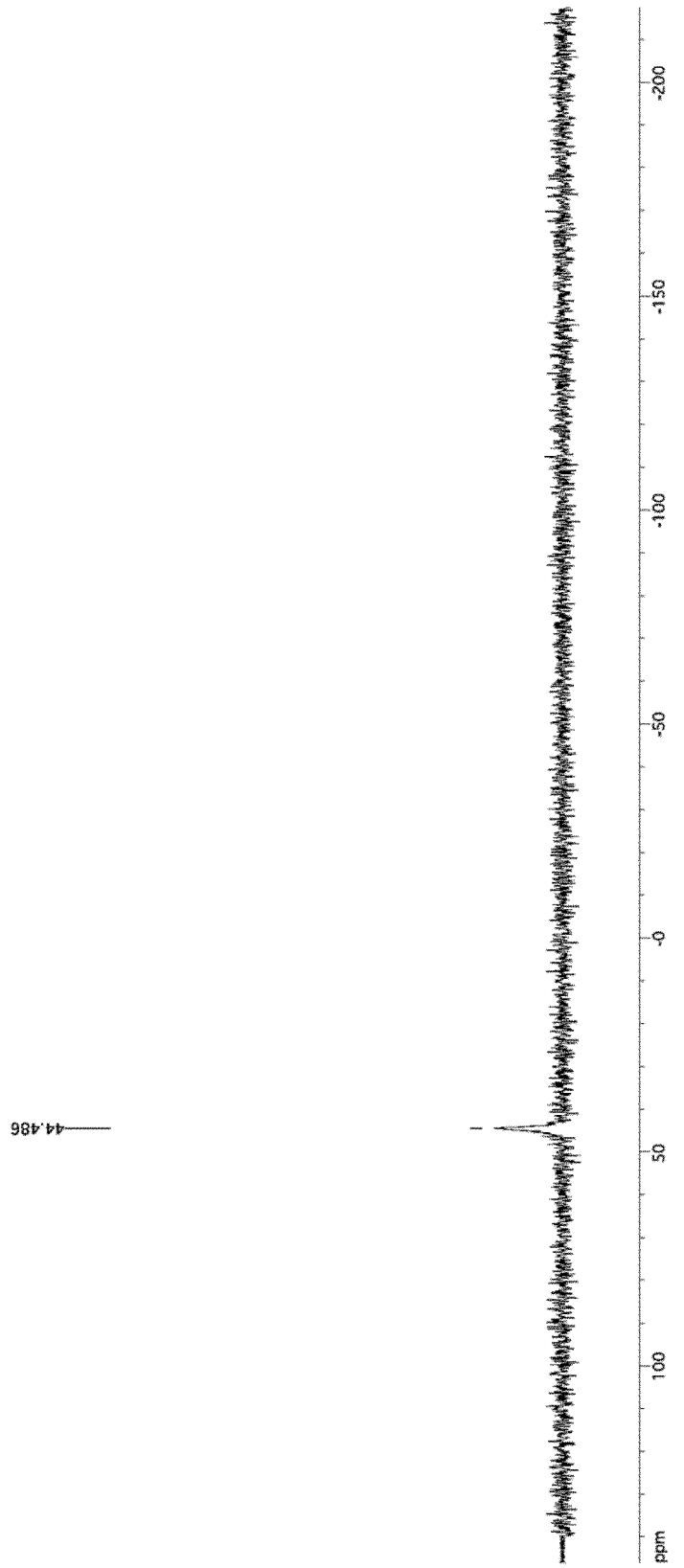
FIG. 2 shows $^1$H-NMR and $^{31}$P-NMR of compound (IIa).
Figure 2:
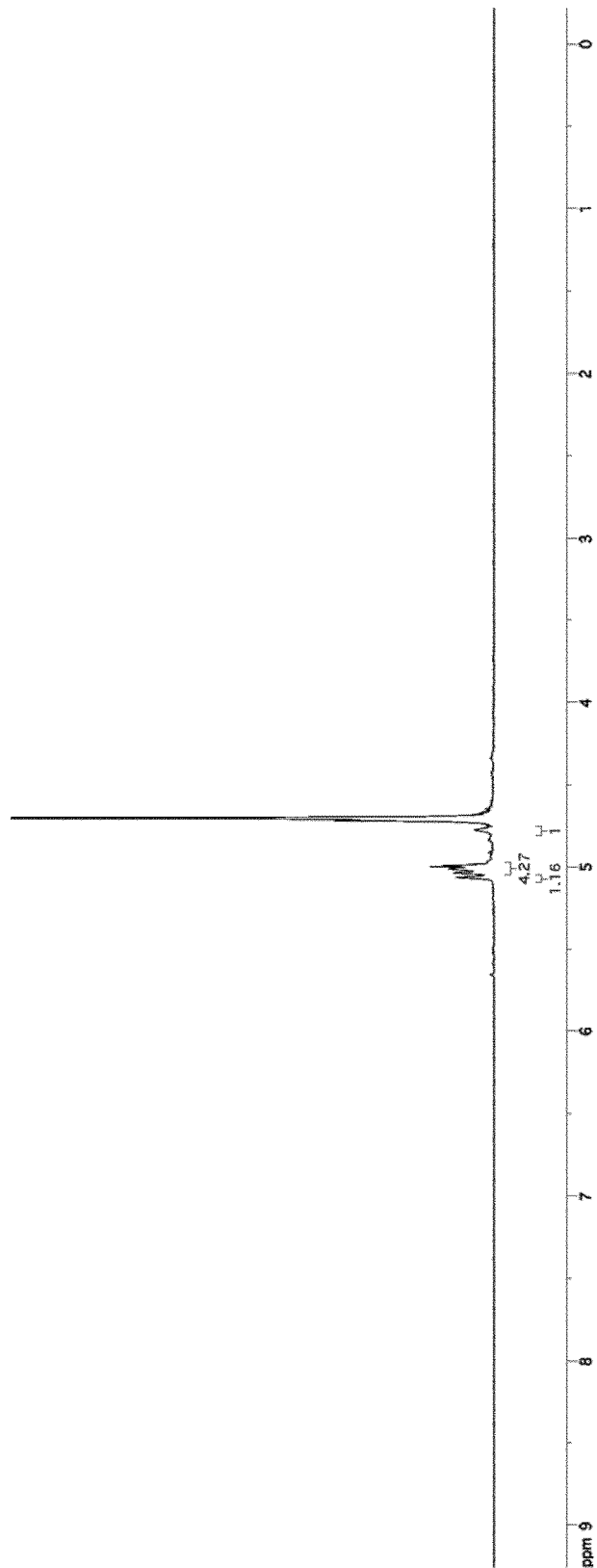

$^{1}$H-NMR and $^{31}$P-NMR results are shown in FIG. 2.

Example 2: Comparison of Cleavage Efficiency

IP6, activator compound (IIa) and IP2S4 were compared with regard to the extent of cleavage of TcdB (FIG. 1). The compound to be tested was added at 1 mM to 150 ng toxin B in presence or absence of 10 mM Ca$^{2+}$ in 100 mM Tris pH7.4 and incubated for 3 h at 37° C. Cleaved protein fragments were separated by SDS-PAGE and visualized by silver staining. The extent of cleavage was quantified from protein band intensities using the ImageJ software package. Signals were normalized to cleavage of positive and negative controls.

Figure 3:
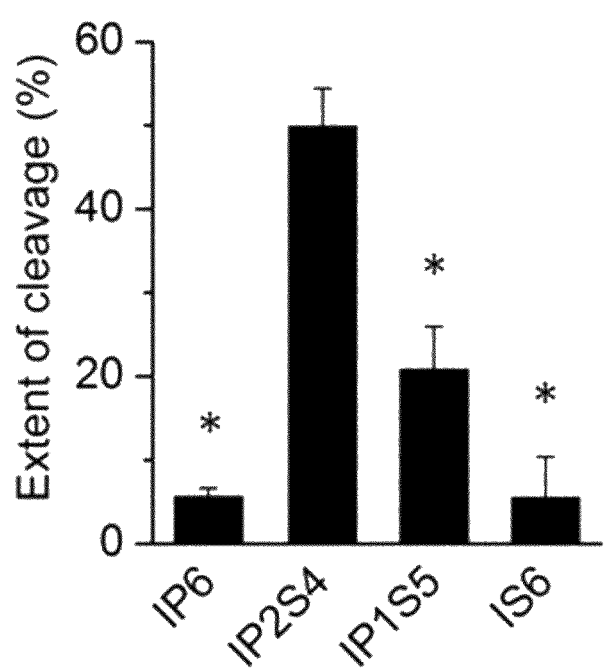
FIG. 3 shows the extent of TcdB cleavage in presence of 10 mM $CaCl_2$) for inositol hexaphosphate (IP6), inositol hexasulphate (IS6), and two mixed phosphate-sulfate compounds.

The results show that the di-thiophosphate-tetra-sulfate inositols are surprisingly superior even in comparison to di-phosphate-tetra-sulfate inositols, which in turn are significantly superior to the inositolhexasulfate and inositol hexaphosphate previously published (FIG. 3 and comparative example 3).

Example 3 (Comparative): P2S4 Inositol, IP6 and IS6 Cleavage Efficiency

Samples were prepared and processed as described in example 2. Error bars show s.d.; Asterisk indicates statistical difference compared to IP2S4 (P<0.05); n=3.

Methods:

Analogue Solubility Measurements by ICP-MS.

100 µM solutions of inositol hexakisphosphate (IP6) analogues with or without 10 mM CaCl$_2$) were prepared in 10 mM tris pH 7.4 and incubated with agitation for 2 h at 37° C. The solutions were immediately filtered through 0.2 µm nylon filters equilibrated to 37° C. The phosphorous content in each filtrate was determined by inductively coupled plasma-mass spectrometry (ICP-MS). The values obtained were divided by the number of phosphates in each IP6 analogue to determine the concentration of the compound in the solutions.

Free Calcium Ion Quantification.

A fresh 1 mM solution of murexide (Merck, Germany) was 10 prepared in 10 mM tris pH 7.4. For each IP6 analogue, samples containing 0.5 mM analogue, murexide and CaC12 in 50 µL 10 mM tris were prepared in triplicate. After 5 min incubation at room temperature, the samples were centrifuged at 20,000 g for 2 min and the upper 40 µL of the supernatant transferred to a 384-well plate. Samples without IP6 analogue containing CaC12 ranging from 1 mM or 20 µM, and 20 mM were also prepared and 15 used for calibrating each experiment. The absorbance was measured at 474 nm and 544 nm and the data analyzed as reported by Ohnishi. [*Anal. Biochem.* 85, 165 (1978)] The experiment was repeated in triplicate.

Cleavage Assays with Holotoxin.

1 mM IP6 analogues were equilibrated with 10 mM CaCl$_2$) in 100 mM tris pH 7.4 for 15 min at 37° C. before addition of 150 ng TcdB (TgcBiomics, Germany) in a total volume of 20 µL. A negative control (no IP6, 10 mM CaCl$_2$)) and a positive control (1 mM IP6) were also included on every gel. The reaction mixtures were incubated for 3 h at 37° C. and then placed on ice. Laemmli sample buffer (5x) was added to stop the reactions and 10 mM EDTA was added to the samples containing CaCl$_2$) before heating at 95° C. for 3 minutes. The cleavage products were visualized by SDS-PAGE (using 15-well 8% acrylamide Precise™ Tris-Glycine gels, ThermoScientific, USA) followed by silver staining according to a modified Vorum protocol [*Proteomics* 1, 1359 (2001)] with the thiosulphate sensitization step extended to 10 min. The linearity of the staining protocol was verified with serial dilutions of TcdB starting at 160 ng/lane down to 20 ng/lane. The band intensities were quantified as described for the cleavage assays with recombinant toxin. The experiment was done in triplicate.

The invention claimed is:

1. A compound characterized by the general formula (I)

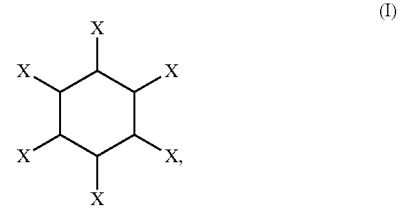

wherein two out of six X are OPSO$_2^{2-}$ and the remaining X are OSO$_3^{-}$.

2. The compound according to claim 1, characterized by the formula (IIa) or (IIb)

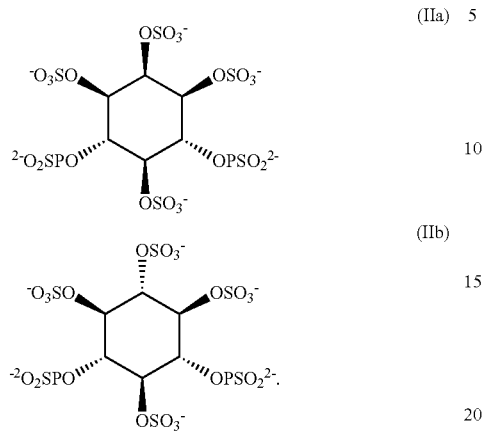

3. A compound according to claim 1 for use in the therapy or prevention of *C. difficile* infection or in the prevention or therapy of symptoms associated with *C. difficile* infection.

4. A dosage form comprising the compound according to claim 1.

5. A compound according to claim 2 for use in the therapy or prevention of *C. difficile* infection or in the prevention or therapy of symptoms associated with *C. difficile* infection.

6. A dosage form comprising the compound according to claim 2.

* * * * *